United States Patent [19]

Nakano et al.

[11] Patent Number: 5,066,722

[45] Date of Patent: Nov. 19, 1991

[54] HEAT-LATENT CURING CATALYST AND RESIN COMPOSITIONS CONTAINING THE SAME

[75] Inventors: Shinji Nakano, Takatsuki; Hiroharu Ohsugi, Hirakata; Satoshi Urano, Tanabecho; Masamichi Furukawa, Osakasayama; Ryozo Takagawa, Toyonaka; Yoshio Eguchi, Ikeda; Takeshi Endo, Yokohama, all of Japan

[73] Assignee: Nippon Paint Co., Ltd., Osaka, Japan

[21] Appl. No.: 485,897

[22] Filed: Mar. 1, 1990

[30] Foreign Application Priority Data

Mar. 3, 1989 [JP] Japan ................................. 1-52674
Mar. 3, 1989 [JP] Japan ................................. 1-52675
Mar. 29, 1989 [JP] Japan ................................. 1-79469
Apr. 25, 1989 [JP] Japan ............................... 1-106737

[51] Int. Cl.$^5$ ...................... C08L 61/00; C08L 61/20; C08L 29/02
[52] U.S. Cl. ................... 525/162; 525/518; 525/519; 525/509
[58] Field of Search ............... 525/549, 518, 519, 162

[56] References Cited

U.S. PATENT DOCUMENTS

| | | | |
|---|---|---|---|
| 3,365,414 | 1/1968 | Fisk et al. | 525/519 |
| 3,474,054 | 10/1969 | White | 528/254 |
| 3,901,840 | 8/1975 | Irvin et al. | 525/163 |
| 4,431,774 | 2/1984 | Felder-Schraner et al. | 525/509 |

Primary Examiner—Melvyn I. Marquis
Assistant Examiner—W. R. H. Clark
Attorney, Agent, or Firm—Millen, White & Zelano

[57] ABSTRACT

Benzylpyridinium or benzylammonium salts of a benzenesulfonate anion are useful as a proton-donating curing catalyst ion a resinous system capable of curing in the presence of such a catalyst. The catalyst is characterized by its heat-latent nature and thus does not impair the storage stability of the resinous system at an ambient temperature.

2 Claims, No Drawings

HEAT-LATENT CURING CATALYST AND RESIN COMPOSITIONS CONTAINING THE SAME

BACKGROUND OF THE INVENTION

This invention relates to a novel class of curing catalysts having a heat-latency, i.e. which are normally inactive but are capable of initiating a curing reaction only at an elevated temperature. The invention also relates to heat-curable resin compositions containing these catalyst which are useful for the preparation of coatings, adhesives, printing inks and other compositions.

In a heat-curable coating system utilizing a proton-donating aromatic sulfonate catalyst, it is imperative to block the sulfonate catalyst with a volatile amine for preventing a premature curing reaction from occuring during storage.

The amine blocked sulfonate catalyst releases a proton according to the following scheme:

$$RSO_3^-\cdot H^+N(R)_3 \rightleftharpoons RSO_3^- + H^+N(R)_3 \rightleftharpoons$$

$$RSO_3^- + H^+ + N(R)_3$$

Accordingly, when it is desired for the sulfonate to exhibit its function at a relatively low temperature, the amine-to-sulfonic acid ratio must be decreased. This increases the amount of free sulfonic acid with the result being decrease in the storage stability of the entire system. Conversely, if the amine-to-sulfonic acid ratio is increased so as to enhance the storage stability, the amount of amine sulfonate salt increases accordingly. This requires the use of higher curing temperatures than desirable so that the sulfonate catalyst functions to its fullest extent. Thus, the curability of a curable system utilizing the amine blocked sulfonate catalyst is generally not compatible with the storage stability thereof.

Accordingly, a strong need exists for a proton-donating catalyst which obviate the above defects.

SUMMARY OF THE INVENTION

In one aspect, the present invention provides a compound of the formula:

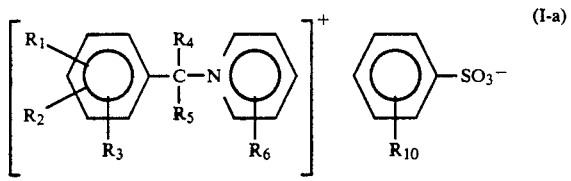

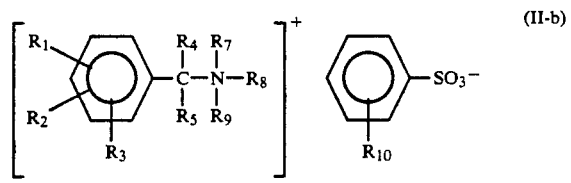

wherein $R_1$, $R_2$, $R_3$ and $R_6$ are each H, halogen, an alkyl, an alkoxy, nitro, amino, an alkylamino, cyano, an alkoxycarbonyl or carbamoyl; $R_4$ and $R_5$ are each H, an alkyl or halogen; $R_7$, $R_8$ and $R_9$ are each an alkyl, an alkenyl or phenyl which may be substituted with nitro, cyano, amino, halogen, an alkyl or a dialkylamino; and $R_{10}$ is H or an alkyl.

In another aspect, the present invention provides a heat-curable resin composition comprising an amount of the above benzylpyridinium sulfonate or benzylammonium sulfonate compound effective to initiate the curing reaction of the composition at an elevated temperature.

The above benzylpyridinium sulfonate or benzylammonium sulfonate compound may be utilized in any one of the following systems:

I. Systems containing a film-forming, hydroxy group-containing resin and a melamine resin;
II. Systems capable of curing through a self-condensation reaction of an alkoxysilyl group-containing resin; and
III. Systems capable of curing through a co-condensation reaction of an alkoxysilyl group-containing resin and a hydroxy group-containing resin.

DETAILED DISCUSSION

1. Heat-Latent Curing Catalyst

The benzylpyridinium sulfonate compound of the formula

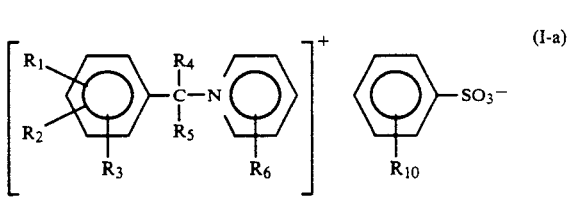

may be synthesized by reacting a corresponding benzyl halide of the formula II:

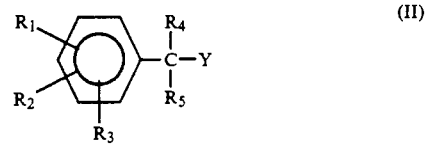

wherein Y is a halogen atom, with a pyridine compound III-a of the formula:

and then reacting the resulting benzylpyridium halide with a corresponding alkali metal benzenesulfonate to metathetically produce the compound I-a.

Similarly, the benzylammonium sulfonate compound of the formula I-b:

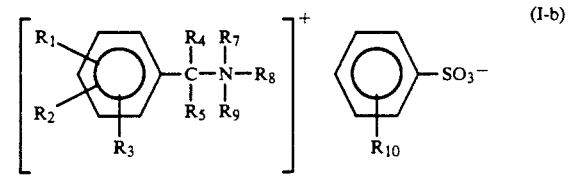

may be synthesized by reacting the benzyl halide (II) with a tertiary amine of the formula III-b:

and then reacting the resulting benzylammonium halide with a corresponding alkali metal benzenesulfonate.

The compounds of the formula I-a or I-b are thermally cleaved at an elevated temperature to produce a benzyl cation of the formula:

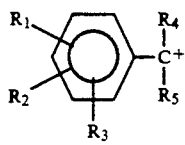

which, in turn, reacts with H₂O or a hydroxy group to produce a proton. However, these compounds are substantially inactive at a temperature below their cleaving points. Therefore, with this type of heat-latent catalyst, the storage stability of a heat-curable resin composition becomes compatible with itse curability.

2. Heat-Curable Resin Compositions

I. Systems containing melamine resins

Melamine resin-containing coating compositions or enamels are well-known in the coating industry.

These compositions usually contain a proton-donor such as p-toluenesulfonic acid for catalyzing the cross-linking reaction with the melamine resin. Since the addition of a free acid to the composition tends to cause gelling of the entire composition upon storage, the catalyst is blocked partially or totally in its acid function with an amine which is volatile at the curing temperature of the composition. However, the curability of this type of composition is generally not compatible with the storage stability thereof.

The use of the heat-latent catalyst of the present invention overcomes this problem. The catalyst is substantially inactive until a critical temperature is reached. However, a carbonium cation is liberated from the catalyst upon heating to a predetermined temperature and a proton is generated by the reaction of the carbonium cation with water or a hydroxy group-containing compound contained in the composition. This enables for the curability and storage stability of the composition to be compatible.

Various film-forming resins are used in the coating industry in combination with a melamine resin. Examples thereof include polyester resins, polylactone resins, epoxy resins, acrylic resins and the like.

Polyester resins are prepared by the condensation reacation of a polycarboxylic acid or its anhydride with a polyhydric alcohol. Any polyester resin having a hydroxy function at the terminal and/or middle of the polyester chain may be cross-linked with the melamine resin.

Hydroxy terminated polylactone resins may also be cross-linked with the melamine resin.

Epoxy resins having an epoxide function and a hydroxy function at the terminal and the middle of the molecule respectively such as bisphenol epoxy resins and novolac epoxy resins may be used in combination with the melamine resin.

Acrylic resins containing a plurality of hydroxy functions may be prepared by copolymerizing a hydroxy group-containing acrylic monomer such as 2-hydroxyethyl (meth)acrylate with one or more comonomers such as alkyl (meth)acrylates, e.g. methyl (meth)acrylate, butyl (meth)acrylate, isobutyl (meth)acrylate and 2-ethylhexyl (meth)acrylate; styrene or its derivatives; (meth)acrylonitrile; vinyl acetate and the like.

Melamine resins are prepared by reacting a triazine compound such as melamine, acetoguanamine or benzoguanamine with formaldehyde, and optionally etherifying the methylol function of the resulting condensate partially or totally with a lower alkanol such as methanol or butanol.

Thermosetting resin compositions comprising a hydroxy group-containing, film-forming resin and a melamine resin are well-known in the coating industry. Except for the use of the above-discussed heat-latent catalyst the composition of the present invention may be otherwise identical to these known compositions.

The weight ratio of the hydroxy group-containing, film-forming resin to the melamine resin ranges between 50:50 to 95:5 on the solid content basis.

The composition of this invention contains from 0.01 to 10%, preferably from 0.05 to 5% by weight of the resin solid content of the catalyst of the formula I-a or I-b. If the amount of the catalyst is deficient, the curability of the composition is not satisfactory. Conversely, excessive use of the catalyst adversely affects the physical properties of cured composition such as dark appearance and decreased water resistance.

The composition may contain convenational additives such as pigments, fillers and the like depending upon its intended use.

II. Systems utilizing the self-condensation or co-condensation reaction of alkoxysilyl groups Japanese Patent Publication No. 33512/88 discloses a curable resin composition containing a vinyl polymer having a plurality of alkoxysilyl group-containing side chains, a polyhydroxy compound and a curing catalyst. It is believed that the composition cures through a self-condensation reaction between two alkoxysilyl groups:

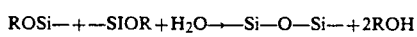

ROSi—+—SIOR+H₂O→—Si—O—Si—+2ROH as well as a co-condensation reaction of an alkoxysilyl group and a hydroxy group:

ROSi—+HO—C——Si—O—C—+ROH

A variety of catalysts are disclosed as being capable of catalyzing the above reactions. These include amines such as butylamine, dibutylamine, t-butylamine, ethylenediamine and the like; organic metal compounds such as tetraisopropyl titanate, tetrabutyl titanate, tin octate, lead octate, zinc octate, calcium octate, dibutyltin diacetate, dibutyltin dioctate, dibutyltin dilaurate and the like; and acid catalysts such as p-toluenesulfonic acid, trichloroacetic acid and the like. The composition containing these catalysts is curable at room temperature. As is self-explanatory from this fact, the composition cannot be stored for a long period of time while containing the curing catalyst. When a long term storage is desired, it is necessary to store the catalyst and the resin component separately and mix the two components immediately prior to use. This is inconvenient in practice and requires to use within a pot life. Another approach includes to reduce the amount of catalyst and blocking the amine or acid catalyst with a suitable acid or amine. Unfortunately they all have been proven unsatisfactory in terms of film properties, storage stabilities and the like.

Similar to the melamine resin-containing composition, the use of the heat-latent catalyst of the present invention in the above-mentioned system overcomes these problems.

Examples of film-forming resins containing a plurality of alkoxysilyl groups include the following:

(1) Acrylic resins containing alkoxysilyl groups

A monomer having both an ethylenically unsaturated function and an alkoxysilyl function in the molecule forms a homopolymer or copolymer containing a plurality of alkoxysilyl groups by itself or with acrylic and/or other comonomers.

A first class of such monomers are alkoxysilylalkyl esters of acrylic or methacrylic acid of the formula:

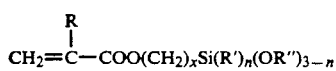

wherein R is H or $CH_3$, R' and R'' are each alkyl, x is an integer, and n is 0, 1 or 2.

Specific examples of these monomers include
γ-methacryloyloxypropyltrimethoxysilane,
γ-methacryloyloxypropylmethyldimethoxysilane,
γ-methacryloyloxypropyldimethylmethoxysilane,
γ-methacryloyloxypropyltriethoxysilane,
γ-methacryloyloxypropylmethyldiethoxysilane,
γ-methacryloyloxypropyldimethylethoxysilane,
γ-methacryloyloxypropyltripropoxysilane,
γ-methacryloyloxypropylmethyldipropoxysilane,
γ-methacryloyloxypropyldimethylpropoxysilane,
γ-methacryloyloxypropyltributoxysilane,
γ-methacryloyloxypropylmethyldibutoxysilane, and
γ-methacryloyloxypropyldimethylbutoxysilane.

A second class of said monomers are adducts of (meth)acrylic acid with an epoxy group-containing alkoxysilane such as
β-glycidylpropyltrimethoxysilane or
β-(3,4-epoxycyclohexyl)ethyltrimethoxysilane.

Another class of alkoxysilyl group-containing monomers are adducts of a hydroxylalkyl (meth)acrylate such as hydroxyethyl (meth)acrylate, hydroxypropyl (meth)acrylate or 4-hydroxybutyl (meth)acrylate with an isocyanotoalkylalkoxysilane of the formula:

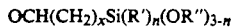

such as γ-isocyanatopropyltrimethoxysilane,
γ-isocyanatopropylmethylmethoxysilane,
γ-isocyanatopropyltriethoxysilane or
γ-isocyanatopropylmethyldiethoxysilane.

A further class of alkoxysilyl group-containing monomers are adducts of glycidyl (meth)acrylate with an aminoalkylalkoxysilane such as
γ-aminopropyltrimethoxysilane,
γ-aminopropyltriethoxysilane,
3-(2-aminoethylamino)propylmethyldimethoxysilane,
3-(2-aminoethylamino)propyltrimethoxysilane,
γ-aminopropyldimethylethoxysilane or
γ-aminopropylmethyldiethoxysilane.

Acrylic and/or other comonomers which may be copolymerized with the alkoxylsilyl group-containing monomer include alkyl (meth)acrylates, (meth)acrylic acid, (meth)acrylonitrile, (meth)arylamide, styrene, vinyl chloride, vinyl acetate and the like.

(2) Silicon-modified epoxy resins

The above-mentioned aminoalkylalkoxysilanes used for preparing an adduct with glycidyl (meth)acrylate may be reacted with an epoxy resin to produce a modified epoxy resin having a plurality of alkoxysilyl groups.

(3) Silicon-modified polyester resins

Polyester resins having a plurality of free carboxyl groups may be modified with the above-mentioned epoxy group-containing alkoxysilane to give silicon-modified polyester resins.

Polyesters having a plurality of hydroxy groups may be reacted with the above-mentioned isocyanatoalkylalkoxysilane to give silicone-modified polyester resins.

Typical examples of hydroxy group-containing resins include polyester resins, polylactone resins, epoxy resins and acrylic resins.

Polyester resins are prepared by the condensation reaction of a polycarboxylic acid or its anhydride with a polyhydric alcohol. Any polyester resin having a hydroxy function at the terminal and/or middle of the polyester chain may be employed.

Hydroxy terminated polylactone resins may also be employed.

Epoxy resins having an epoxide function and a hydroxy function at the terminal and the middle of the molecule respectively, such as bisphenol epoxy resins and novolac epoxy resins may be employed.

Acrylic resins containing a plurality of hydroxy functions may be prepared by copolymerizing a hydroxy group-containing acrylic monomer such as 2-hydroxyethyl (meth)acrylate with one or more comonomers such as alkyl (meth)acrylates, e.g. methyl (meth)acrylate, butyl (meth)acrylate, isobutyl (meth)acrylate and 2-ethylhexyl (meth)acrylate, styrene or its derivatives; (meth)acrylonitrile, vinyl acetate and the like.

Systems utilizing the self-condensation reaction of alkoxysilyl groups contain the above-mentioned silicon-containing resin and from 0.01 to 10%, preferably from 0.05 to 5% by weight of the resin solid content of the compound I-a or I-b.

Systems utilizing the co-condensation of alkoxysilyl group with hydroxy group contain the above-mentioned silicon-containing resin, an amount of hydroxy group-containing resin at a molar ratio of the hydroxy group per alkoxysilyl group of 0.1 to 10, and 0.01 to 10%, preferably from 0.05 to 5% by weight of the resin solid content of the compound I-a or I-b.

If the amount of compound I-a or I-b is deficient, the curability of the composition is not satisfactory. Conversely, excessive addition of the compound I-a or I-b adversely affects the physical properties of cured composition such as dark appearance and decreased water resistance.

The composition may contain conventional additives such as fillers, pigments and the like depending upon its intended use.

The resulting composition has an increased storage stability at room temperature but curable at a temperature above the cleaving point of the compound I-a or I-b. The curing time may vary with the curing temperature but usually within one hour.

The following examples are intended to further illustrate the present invention without limiting thereto. All parts and percents therein are by weight unless otherwise indicated.

EXAMPLES

Part I. Synthesis of Catalysts

Example I-1

N-(4-methoxybenzyl)-4-cyanopyridinium p-dodecylbenzenesulfonate 4,698 g (0.03 mol) of 4-methoxybenzyl chloride and 10.22 g (0.09 mol) of 4-cyanopyridine were reacted in 90 ml of methanol at 40° C. for 3 days. After the reaction, the solvent was evaporated in vacuo and ether was added to the residue to extract unreacted materials in the etherial layer. The residue was dissolved in 30 ml of methanol and 10.44 g (0.03 mol) of sodium p-dodecylbenzene sulfonate was added to the solution. The reaction mixture was then filtered to remove sodium chloride crystals formed and the filtrate was evaporated to obtain the title compound.

NMR: 0.6–1.5 ppm (m, 25H, dodecyl), 3.8 ppm (s, 3H, MeO), 5.8 ppm (s, 2H, CH$_2$), 7.2–7.4 ppm (m, 6H, Ph), 7.5 ppm (d, 2H, Ph), 8.7 ppm (d, 2H, Py), 9.4 ppm (d, 2H, Py)

Examples I-2 to I-38

Analogous to Example I-1, various compounds of the formula I-a listed in the following table were synthesized. Formula I-a:

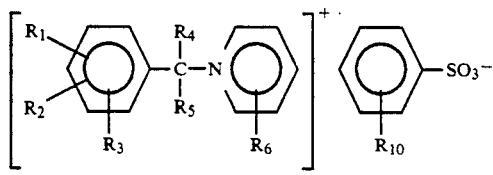

| Example No. | R$_3$ | R$_6$ | R$_{10}$ |
|---|---|---|---|
| I-2 | 4-methybenzyl | 4-cyano | p-dodecyl |
| I-3 | 4-t-butylbenzyl | " | " |
| I-4 | 4-chlorobenzyl | " | " |
| I-5 | 4-nitrobenzyl | " | " |
| I-6 | 4-cholorobenzyl | 2-chloro | " |
| I-7 | 4-methylbenzyl | 4-dimethyl-amino | " |
| I-8 | " | 4-methyl | " |
| I-9 | benzyl | 2-cyano | " |
| I-10 | " | 2-chloro | " |
| I-11 | 2-methylbenzyl | 4-cyano | " |
| I-12 | 2-chlorobenzyl | " | " |
| I-13 | 4-methylbenzyl | 2-methyl | " |
| I-14 | 4-methoxybenzyl | 2-chloro | " |
| I-15 | 4-methylbenzyl | 2-cyano | p-dodecyl |
| I-16 | " | 2-chloro | " |
| I-17 | 2-chloro-6-fluoro-benzyl | 4-cyano | " |
| I-18 | 2-methylbenzyl | 2-cyano | p-dodecyl |
| I-19 | benzyl | 4-cyano | " |
| I-20 | 4-methylbenzyl | H | " |
| I-21 | 2,4-dichlorobenzyl | 4-cyano | " |
| I-22 | 4-nitrobenzyl | 2-methyl | " |
| I-23 | 2-methyl | 4-chloro | p-methyl |
| I-24 | 4-methoxybenzyl | H | " |
| I-25 | benzyl | H | p-dodecyl |

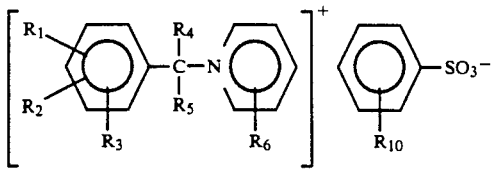

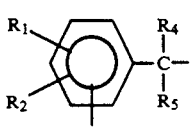

| Example No. | R$_3$ | R$_6$ | R$_{10}$ |
|---|---|---|---|
| I-26 | α,α-dimethylbenzyl | H | p-dodecyl |
| I-27 | " | 4-cyano | " |
| I-28 | " | 2-chloro | " |
| I-29 | " | 2-methyl | " |
| I-30 | " | 2-cyano | " |
| I-31 | " | 4-methyl | " |
| I-32 | α,α-dimethylbenzyl | 4-dimethyl-amino | " |
| I-33 | " | H | p-methyl |
| I-34 | " | 4-methyl | " |
| I-35 | " | 4-dimethyl-amino | " |
| I-36 | α-methylbenzyl | 4-cyano | p-dodecyl |
| I-37 | " | 2-chloro | " |
| I-38 | p-methyl-α-methyl-benzyl | 2-methy | p-methyl |

Example I-39

N-(4-methoxybenzyl)-N,N-dimethylanilinium p-dodecylbenzenesulfonate 4,698 g (0.03 mol) of 4-methoxybenzyl chloride and 3.638 g (0.03 mol) of N,N-dimethylaniline were reacted in 40 mol of methanol at 40° C. for 3 days. After the reaction, the solvent was evaporated in vacuo and ether was added to the residue to extract unreacted materials in the etherial layer. The residue was dissolved in 30 ml of methanol and 10.44 g (0.03 mol) of sodium p-dodecylbenzenesulfonate was added thereto. The reaction mixture was filtered to remove sodium chloride crystals and the filtrate was evaporated to obtain the title compound.

NMR: 0.6–1.5 ppm (m, 25H, dodecyl), 3.6 ppm (s, 6H, Me), 3.8 ppm (s, 3H, MeO), 5.8 ppm (s, 2H, CH$_2$), 7.0 ppm (d, 2H, Ph), 7.2 ppm (m, 11H, Ph)

Examples I-40 to I-71

Analogous to Example I-39, various compounds of the formula I-b listed in the following Table were synthesized. Formula I-b;

| Example No. | $R_1$ $R_2$ $R_3$ ring-$C(R_4)(R_5)$- | $-{}^+N(R_7)(R_8)(R_9)$ | $R_{10}$ |
|---|---|---|---|
| I-40 | 4-methylbenzyl | N,N-dimethyl-anilinium | p-dodecyl |
| I-41 | 4-t-butylbenzyl | N,N-dimethyl-anilinium | " |
| I-42 | 4-chlorobenzyl | N,N-dimethyl-anilinium | " |
| I-43 | 4-nitrobenzyl | N,N-dimethyl-anilinium | " |
| I-44 | 4-chlorobenzyl | N,N-dimethyl-anilinium | p-methyl |
| I-45 | 4-methylbenzyl | N,N-dimethyl-anilinium | " |
| I-46 | " | N,N-dimethyl-N-(m-tolyl)-ammonium | p-dodecyl |
| I-47 | benzyl | N,N-dimethyl-anilinium | " |
| I-48 | " | N,N-dimethyl-N-(p-tolyl)-ammonium | " |
| I-49 | 2-methylbenzyl | N,N-dimethyl-anilinium | " |
| I-50 | 2-chlorobenzyl | N,N-dimethyl-anilinium | p-dodecyl |
| I-51 | 2,3-dimethylbenzyl | N,N-dimethyl-anilinium | " |
| I-52 | 4-methoxybenzyl | N,N-dimethyl-anilinium | p-methyl |
| I-53 | 4-methylbenzyl | N,N-dimethyl-N-(p-tolyl)-ammonium | p-dodecyl |
| I-54 | " | N,N-dimethyl-N-(p-tolyl)-ammonium | p-methyl |
| I-55 | 2-chloro-6-fluorobenzyl | N,N-dimethyl-anilinium | p-dodecyl |
| I-56 | 2-methylbenzyl | N,N-dimethyl-anilinium | p-methyl |
| I-57 | α-methylbenzyl | N,N-dimethyl-anilinium | p-dodecyl |
| I-58 | " | N-2-hydroxyethyl-N,N-dimethylammonium | " |
| I-59 | α-methylbenzyl | N,N,N-trimethylammonium | p-dodecyl |
| I-60 | 4-chloro-α-methylbenzyl | N-2-hydroxyethyl-N,N-dimethylammonium | " |
| I-61 | 4-methyl-α-methylbenzyl | N,N,N-trimethylammonium | " |
| I-62 | α-methylbenzyl | N,N,N-trimethylammonium | p-methyl |
| I-63 | 4-chloro-α-methylbenzyl | N-2-hydroxyethyl-N,N-dimethylammonium | " |
| I-64 | α,α-dimethylbenzyl | N,N-dimethylanilinium | p-dodecyl |
| I-65 | " | N-2-hydroxyethyl-N,N-dimethylammonium | " |
| I-66 | α,α-dimethylbenzyl | N,N,N-triethylammonium | p-dodecyl |
| I-67 | " | N,N,N-trimethylammonium | " |
| I-68 | 4-nitro-α,α-dimethylbenzyl | N,N-dimethyl-anilimium | " |
| I-69 | 4-methyl-α,α-dimethylbenzyl | N-2-hydroxyethyl-N,N-dimethyl-ammonium | " |
| I-70 | α,α-dimethylbenzyl | N-2-hydroxyethyl-N,N-dimethyl-ammonium | p-methyl |
| I-71 | " | N,N,N-triethyl-ammonium | " |

Part II. Production of Vehicle Resins

Polyester Resin

Example II-1

A reaction vessel provided with a heater, stirrer, reflux condenser, water separator, fractional distillation column and thermometer was charged with 36 parts of hexahydrophthalic acid, 42 parts of trimethylolpropane, 50 parts of neopentyl glycol and 56 parts of 1,6-hexanediol. The mixture was heated to 210° C. with stirring. Then the mixture was heated to 230° C. at a constant rate over 2 hours while distilling out water formed as a by-product by the condensation reaction. The reaction was continued at 230° C. until an acid number of 1.0 was reached and stopped by cooling. After the addition of 153 parts of isophthalic acid, the reaction mixture was heated again to 190° C. and thereafter from 190° C. to 210° C. at a constant rate over 3 hours while distilling out formed water. When this temperature was reached, 3 parts of xylene was added and the reaction was continued until an acid number of 5.0 was reached. After cooling, the reaction mixture was diluted with 190 parts of xylene whereupon Polyester solution A was obtained.

Acrylic Resin

Example II-2

A reaction vessel provided with a stirrer, thermometer, reflux condenser, nitrogen gas-introducing tube and dripping funnel was charged with 90 parts of SOLVESSO 100 and heated to 160° C. while introducing nitrogen gas. To the vessel was added dropwise the following monomer mixture at a constant rate:

| | |
|---|---|
| 2-Hydroxyethyl methacrylate | 23.20 parts |
| Methyl methacrylate | 40.15 parts |
| n-Butyl acrylate | 35.65 parts |
| Methacrylic acid | 1.00 parts |
| t-Butylperoxy-2-ethylhexanoate | 10.00 parts |

One hour after the addition, a mixture of 10 parts of xylene and 1 part of t-butylperoxy-2-ethylhexanoate was added dropwise at a constant rate over 30 minutes. The reaction was allowed to proceed to completion for 2 hours and stopped by cooling to give Acrylic Resin A.

Silicon Resins

Example II-3

A reaction vessel used in Example II-2 was charged with 45 parts of xylene and heated to 130° C. while introducing nitrogen gas. To the vessel was added dropwise a mixture of 50 parts of γ-methacryloyloxypropyltrimethoxysilane and 4 parts of t-butylperoxy-2-ethylhexanoate at a constant rate over 3 hours.

30 minutes after the addition, the mixture was cooled to 90° C., and a mixture of 1 part of butylperoxy-2-ethylhexanoate and 5 parts of xylene was added thereto. The reaction was allowed to proceed to completion for additional 2 hours and stopped by cooling to give Silicon Resin A.

Example II-4

Analogous to Example II-3, a mixture of 50 parts of γ-methacryloyloxypropylmethyldimethoxysilane and 4 parts of t-butylperoxy-2-ethylhexanoate was polymerized to give Silicon Resin B.

Example II-5

Analogous to Example II-3, a mixture of 50 parts of γ-methacryloyloxypropyldimethylmethoxysilane and 4 parts of t-butylperoxy-2-ethylhexanoate was polymerized to give Silicon Resin C.

Example II-6

Analogous to Example II-3, a mixture of 50 parts of γ-methacryloyloxypropyltriethoxysilane and 4 parts of t-butylperoxy-2-ethylhexanoate was polymerized to give Silicon Resin D.

Example II-7

Analogous to Example II-3, a mixture of 25 parts of γ-methacryloyloxypropyltriethoxysilane, 25 parts of methyl methacrylate and 4 parts of t-butylperoxy-2-ethylhexanoate was polymerized to give Silicon Resin E.

Example II-8

A reaction vessel provided with a stirrer, thermometer and reflux condenser was charged with 100 parts of Polyester Resin A obtained in Example I-1 and heated to 100° C. After the addition of 0.2 parts of dibutyltin dilaurate, 10 parts of KBK-9007 (chemically γ-isocyanatopropyltrimethoxysilane sold by Shin-Etsu Chemical Co., Ltd.) were added dropwise at a constant rate over 30 minutes and the reaction allowed to proceed to completion for additional 1 hour. After cooling, Silicon Resin F was obtained. The adsorption of NCO group at 1720 cm$^{-1}$ disappeared completely in the IR spectrometry of the resin.

Example II-9

A reaction vessel provided with a stirrer, thermometer and reflux condenser was charged with 100 parts of bisphenol A diglycidyl ether and heated to 150° C. Then 100 parts of γ-aminopropyltrimethoxysilane were added dropwise at a constant rate over 1 hour and allowed to react for additional 1 hour. After cooling, Silicon Resin G was obtained.

Part III. Systems Containing Melamine Resin

Example III-1

70 parts of PLACCEL 308, 30 parts of CYMEL 303 (melamine resin sold by Mitsui Toatsu Chemicals, Inc.) and 2 parts of 1-(4-methylbenzyl)-4-cyanopyridinium p-dodecylbenzenesulfonate were thoroughly mixted. The mixtures was cast on a tinplate and baked at 140° C. The curability and storage stability of the mixture are shown in Table III-1.

Examples III-2 to III-16

Analogous to Example III-1, the following compositions were tested for the curability and storate stability. The results are shown in Table III-1.

Catalyst of the formula:

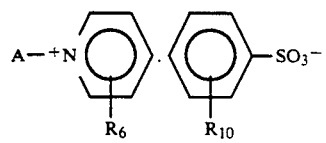

| Example | Catalyst A, $R_6$, $R_{10}$, parts | | Resin, parts | |
|---|---|---|---|---|
| III-2 | 4-chlorobenzyl, 2-CH$_3$, p-dodecyl | 5 | Placcel 308 Cymel 303 | 70 30 |
| III-3 | 2,4-dichlorobenzyl, 2-CH$_3$, p-dodecyl | 2 | Placcel 308 Cymel 303 | 50 50 |
| III-4 | 2-methylbenzyl, 2-CH$_3$, p-dodecyl | 2 | Polyester A (solid content) Cymel 303 | 90 10 |
| III-5 | 2,4-dimethylbenzyl, 2-Cl, p-dodecyl | 1 | Polyester A (solid content) Yuban 20SE 1) (solid content) | 60 40 |
| III-6 | 4-methoxybenzyl, 3-Cl, p-CH$_3$ | 2 | Polyester A (solid content) Yuban 20SE (solid content) | 70 30 |
| III-7 | α, α-dimethylbenzyl, H, p-dodecyl | 2 | Polyester A (solid content) Yuban 20SE (solid content) | 60 40 |
| III-8 | α-methylbenzyl, H, p-dodecyl | 2 | Polyester A (solid content) Yuban 20S (solid contnet) | 70 30 |
| III-9 | benzyl, 2-methyl, p-dodecyl | 2 | Acrylic A (solid content) Cymel 303 | 90 10 |
| III-10 | 2-chlorobenzyl, 2-CH$_3$, p-CH$_3$ | 0.1 | Acrylic A (solid content) Yuban 20SE (solid content) | 60 40 |
| III-11 | 4-methoxybenzyl, 4-chloro, p-CH$_3$ | 2 | Acrylic A (solid content) Yuban 20SE (solid content) | 70 30 |
| III-12 | α-methylbenzyl, 4-CN, p-dodecyl | 2 | Acrylic A (solid content) Cymel 303 | 90 10 |
| III-13 | α, α-dimethylbenzyl, 4-CH3, p-dodecyl | 2 | Acrylic A (solid content) Yuban 20SE (solid content) | 70 30 |
| III-14 (for comparison) | triethylamine p-toluenesulfonate | 2 | Placcel 308 Cymel 303 | 70 30 |
| III-15 (for comparison) | pyridine p-dodecylbenzenesulfonate | 2 | Polyester A (solid content) Cymel 303 | 90 10 |

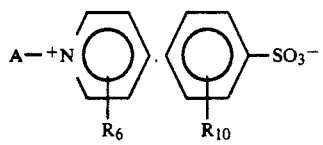

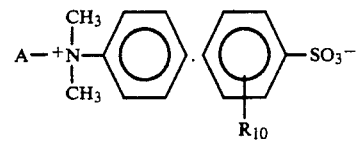

| Example | Catalyst A, $R_6$, $R_{10}$, parts | Resin, parts | |
|---|---|---|---|
| III-16 (for comparison) | pyridine p-toluenesulfonate | 2 | Acrylic A (solid content) 60<br>Yuban 20SE (solid content) 40 |

(1) Melamine resin sold by Mitsui-Toatsu Chemicals, Inc.

| Example | Catalyst A, $R_{10}$, parts | | Resin, parts | |
|---|---|---|---|---|
| | p-dodecyl | | (solid content)<br>Yuban 20SE (solid content) | 40 |
| III-25 | #III-24 | 2 | Acrylic D (solid content)<br>Yuban 20S (solid content) | 70<br>30 |

TABLE III-1

| | Example | | | | | | | | | | | | | (for comparison) | | |
|---|---|---|---|---|---|---|---|---|---|---|---|---|---|---|---|---|
| | III-1 | III-2 | III-3 | III-4 | III-5 | III-6 | III-7 | III-8 | III-9 | III-10 | III-11 | III-12 | III-13 | III-14 | III-15 | III-16 |
| Durability[1] | ⊙ | ⊙ | ○ | ○ | ○ | ⊙ | ○ | ⊙ | ⊙ | ○ | ○ | ⊙ | ○ | ○ | ○ | ⊙ |
| Storage Stability[2] | ○ | ⊙ | ⊙ | ⊙ | ○ | ⊙ | ○ | ○ | ⊙ | ⊙ | ○ | ○ | ⊙ | △ | x | |

[1] Film appearance after the MEK rubbing test (100 reciprocations).
⊙: No change; ○: Slightly changed; △: Whitening; x: Dissolved
[2] Viscosity increase after storing in a closed system at 40° C. for 2 weeks.
⊙: No increase; ○: Slightly increased; △: Increased; x: Gelling

Examples III-17 to III-21

Analogous to Example III-1, the following compositions were tested for the curability and storage stability. The results are shown in Table III-2.

Catalyst of the formula unless otherwise indicated:

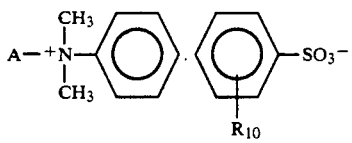

| Example | Catalyst A, $R_{10}$, parts | | Resin, parts | |
|---|---|---|---|---|
| III-17 | 4-methylbenzyl, p-dodecyl | 2 | Placcel 308<br>Cymel 303 | 70<br>30 |
| III-18 | 4-chlorobenzyl, p-dodecyl | 5 | Placcel 308<br>Cymel 303 | 70<br>30 |
| III-19 | 2,4-dichlorobenzyl, p-dodecyl | 2 | Placcel 308<br>Cymel 303 | 50<br>50 |
| III-20 | #III-20 | 2 | Polyester A (solid content)<br>Cymel 303 | 90<br>10 |
| III-21 | 2,4-dimethylbenzyl, p-CH$_3$ | 1 | Polyester A (solid content)<br>Yuban 20S (solid content) | 60<br>40 |
| III-22 | 4-methoxybenzyl, p-CH$_3$ | 0.05 | Polyester A (solid content)<br>Yuban 20S (solid content) | 70<br>30 |
| III-23 | α,α-dimethylbenzyl, p-dodecyl | 2 | Polyester A | 60 |
| III-25 | benzyl, p-dodecyl | 0.5 | Acrylic A (solid content)<br>Cymel 303 | 90<br>10 |
| III-26 | 2-chlorobenzyl, p-CH$_3$ | 0.1 | Acrylic A (solid content)<br>Yuban 20SE (solid content) | 60<br>40 |
| III-27 | 4-methoxybenzyl, p-CH$_3$ | 2 | Acrylic A (solid content)<br>Yuban 20SE (solid content) | 70<br>30 |
| III-28 | α-methybenzyl, p-dodecyl | 2 | Acrylic A (solid contnet)<br>Cymel 303 | 90<br>10 |
| III-29 | α,α-dimethylbenzyl, p-dodecyl | 2 | Acrylic A (solid content)<br>Yuban 20SE (solid content) | 70<br>30 |

III-20: N-2-methylbenzyl-N,N-diethylanilinium p-dodecylbenzenesulfonate.
III-24: N-α-methylbenzyl-N-2-hydroxyethyl-N,N-dimethylammonium p-dodecylbenzenesulfonate.

TABLE III-2

| | Example | | | | | | | | | | | | |
|---|---|---|---|---|---|---|---|---|---|---|---|---|---|
| | III-17 | III-18 | III-19 | III-20 | III-21 | III-22 | III-23 | III-24 | III-25 | III-26 | III-27 | III-28 | III-29 |
| Curability[1] | ⊙ | ○ | ○ | ○ | ⊙ | ○ | ⊙ | ○ | ⊙ | ○ | ○ | ○ | ⊙ |
| Storage Stability[2] | ○ | ⊙ | ⊙ | ⊙ | ○ | ⊙ | ○ | ⊙ | ○ | ⊙ | ○ | ○ | ○ |

[1] Film appearance after the MEK rubbing test (100 reciprocations).
⊙: No change; ○: Slightly changed; △: Whitening; x: Dissolved
[2] Viscosity increase after storing in a closed system at 40° C. for 2 weeks.
⊙: No change; ○: Slightly increased; △: Increased; x: Gelling

Part IV. Alkoxysilyl Group Self- or Co-condensation Systems

Example IV-1

100 parts of Acrylic Resin A, 30.9 parts of Silicon Resin A, 5 parts of methanol and 2.62 parts of 1-benzyl-4-cyanopyridinium p-dodecylbenzenesulfonate were thoroughly mixed. The mixture was cast on a steel plate, allowed to set for 2 hours and baked at 140° C. for 30 minutes. The curability and storage stability of the mixture are shown in Table IV-1.

Example IV-2 to IV-20

Analogous to Example IV-1, the following compositions were tested for the curability and storage stability. The results are shown in Table IV-1.

Initiator of the formula:

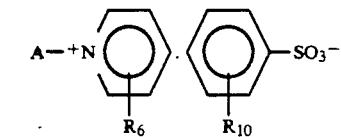

| Example | Catalyst A, $R_6$, $R_{10}$, parts | | Resin, parts | |
|---|---|---|---|---|
| IV-2 | 2-chloronenzyl, 4-CN, p-dodecyl | 2.58 | Acrylic A<br>Silicon B<br>Methanol | 100<br>28.9<br>5 |
| IV-3 | 2,4-dichlorobenzyl, 4-CN, p-dodecyl | 2.54 | Acrylic A<br>Silicon C<br>Methanol | 100<br>26.9<br>5 |
| IV-3 | 2,4-dichlorobenzyl, 4-CN, p-dodecyl | 2.54 | Acrylic A<br>Silicon C<br>Methanol | 100<br>26.9<br>5 |
| IV-4 | 2-methylbenzyl, 2-CN, p-dodecyl | 2.72 | Acrylic A<br>Silicon C<br>Methanol | 100<br>36.2<br>5 |
| IV-5 | 4-nitrobenzyl, 2-CH$_3$, p-dodecyl | 2.87 | Acrylic A<br>Silicon E<br>Methanol | 100<br>43.4<br>5 |
| IV-6 | α-methylbenzyl, 4-Cl, p-dodecyl | 2.62 | Acrylic A<br>Cymel 303<br>Silicon A<br>Methanol | 100<br>20.6<br>10.3<br>5 |
| IV-7 | α-methylbenzyl, 4-CN, p-dodecyl | 2.58 | Acrylic A<br>Silicon B<br>Methanol | 100<br>28.9<br>5 |
| IV-8 | α, α-dimethylbenzyl, p-dodecyl | 2.54 | Acrylic A<br>Silicon C | 100<br>26.9 |
| IV-9 | α-methylbenzyl, 4-F, p-CH$_3$ | 2.87 | Polyester A<br>Silicon F<br>Methanol | 100<br>30<br>5 |
| IV-10 | 4-methoxybenzyl, H, p-CH$_3$ | 2.87 | Polyester A<br>Silicon G<br>Methanol | 100<br>28.9<br>5 |
| IV-11 | benzyl, H, p-CH$_3$ | 2.62 | Acrylic A<br>Silicon A<br>Cymel 303<br>Methanol | 100<br>10.3<br>20.6<br>5 |
| IV-12 | 2-chlorobenzyl, 4-CN, p-dodecyl | 0.5 | Silicon A<br>Methanol | 100<br>5 |
| IV-13 | 2-chlorobenzyl, 4-CN, p-dodecyl | 0.5 | Silicon B<br>Methanol | 100<br>5 |
| IV-14 | 2-chlorobenzyl, 4-CN, p-dodecyl | 0.5 | Silicon C<br>Methanol | 100<br>5 |
| IV-15 | 2-chlorobenzyl, 4-CN, p-dodecyl | 0.5 | Silicon F<br>Methanol | 100<br>5 |
| IV-16 | α, α-dimethylbenzyl, 4-Cl, p-dodecyl | 2.58 | Silicon B<br>Methanol | 100<br>5 |
| IV-17 | Pyridine p-dodecyl- | 2 | Acrylic A | 100 |

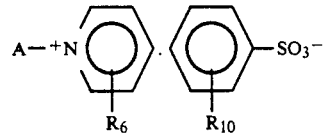

| Example | Catalyst A, $R_6$, $R_{10}$, parts | | Resin, parts | |
|---|---|---|---|---|
| (for comparison) | benzenesulfonate | | Silicon A<br>Methanol | 30.9<br>5 |
| IV-18 (for comparison) | triethylamine p-dodecyl-benzenesulfonate | 2 | Acrylic A<br>Silicon A<br>Methanol | 100<br>30.9<br>5 |
| IV-19 (for comparison) | None | | Silicon A<br>Methanol | 100<br>5 |
| IV-20 (for comparison) | triethylamine p-dodecyl-benzenesulfonate | 2 | Silicon A<br>Methanol | 30.9<br>5 |

TABLE IV-1

| | Example | | | | | | | | | |
|---|---|---|---|---|---|---|---|---|---|---|
| | IV-1 | IV-2 | IV-3 | IV-4 | IV-5 | IV-6 | IV-7 | IV-8 | IV-9 | IV-10 |
| Curability[1] | ⊚ | ⊚ | ⊚ | ⊚ | ⊚ | ⊚ | ⊚ | ⊚ | ⊚ | ⊚ |
| Storage stability[2] | ○ | ○ | ○ | ○ | ○ | ○ | ○ | ○ | ○ | ○ |

| | Example | | | | | | | | | |
|---|---|---|---|---|---|---|---|---|---|---|
| | IV-11 | IV-12 | IV-13 | IV-14 | IV-15 | IV-16 | IV-17 | IV-18 | IV-19 | IV-20 |
| Curability[1] | ⊚ | ⊚ | ⊚ | ⊚ | ⊚ | ⊚ | ⊚ | ○ | x | ⊚ |
| Storage stability[2] | ○ | ○ | ○ | ○ | ○ | ○ | x | Δ | ○ | x |

[1] Film appearance after the MEK rubbing test (100 reciprocations).
⊚: No change; ○: Slightly changed; Δ: Whitening; x: Dissolved
[2] Viscosity increase after storing in a closed system at 40° C. for 2 weeks.
⊚: No change; ○: Slightly increased; Δ: increased; x: Gelling;

Examples IV-21 to IV-34

Analogous to Example IV-1, the following compositions were tested for the curability and storage stability. The results are shown in Table IV-2.

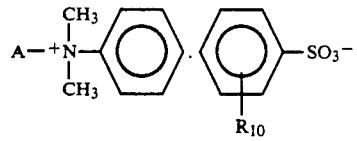

| Example | Catalyst A, $R_{10}$, parts | | Resin, parts | |
|---|---|---|---|---|
| IV-21 | benzyl, p-dodecyl | 2.62 | Acrylic A<br>Silicon A<br>Methanol | 100<br>30.9<br>5 |
| IV-22 | 2-chlorobenzyl, p-dodecyl | 2.58 | Acrylic A<br>Silicon B<br>Methanol | 100<br>28.9<br>5 |
| IV-23 | 2,4-dichlorobenzyl, p-dodecyl | 2.54 | Acrylic A<br>Silicon C<br>Methanol | 100<br>26.9<br>5 |
| IV-24 | #II-24 | 2.72 | Acrylic A<br>Silicon D<br>Methanol | 100<br>36.2<br>5 |
| IV-25 | 4-nitrobenzyl, p-dodecyl | 2.87 | Acrylic A<br>Silicon E<br>Methanol | 100<br>43.4<br>5 |
| IV-26 | #IV-26 | 2.87 | Acrylic A<br>Silicon F | 100<br>30 |

-continued

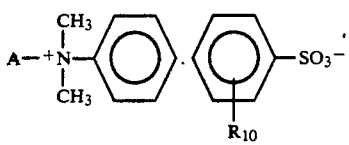

| Example | Catalyst A, $R_{10}$, | parts | Resin, parts | |
|---|---|---|---|---|
| IV-27 | 4-methoxybenzyl, p-dodecyl | 2.87 | Methanol<br>Polyester A<br>Silicon G<br>Methanol | 5<br>100<br>18<br>5 |
| IV-28 | #IV-28 | 2.62 | Acrylic A<br>Cymel 303<br>Silicon A<br>Methanol | 100<br>20.6<br>10.3<br>5 |
| IV-29 | #IV-29 | 2.85 | Acrylic A<br>Silicon B<br>Methanol | 100<br>28.9<br>5 |
| IV-30 | α-methylbenzyl, p-dodecyl | 2.54 | Acrylic A<br>Silicon C<br>Methanol | 100<br>26.9<br>5 |
| IV-31 | α,α-dimethyl-4-chloro-benzyl, p-dodecyl | 2.58 | Silicon B<br>Methanol | 100<br>5 |
| IV-32 | benzyl, p-dodecyl | 0.5 | Silicon A<br>Methanol | 100<br>5 |
| IV-33 (for comparison) | triethylamine p-toluenesulfonate | 2.58 | Silicon A<br>Methanol | 100<br>5 |
| IV-34 (for comparison) | pyridine p-toluenesulfonate | 2.62 | Acrylic A<br>Silicon A<br>Methanol | 100<br>30.9<br>5 |

IV-24: N-2-Methylbenzyl-N-m-tolyl-N,N-dimethylammonium p-dodecylbenzenesulfonate.
IV-26: N-2-Methylbenzyl-N,N-diethylanilinium p-dodecylbenzene sulfonate.
IV-28: N-α-methylbenzyl-N-2-hydroxyethyl-N,N-dimethylammonium p-dodecylbenzenesulfonate.
IV-29: N-α-methylbenzyl-N,N,N-trimethylammonium p-dodecylbenzenesulfonate.

TABLE IV-2

| | Example | | | | | | | | | | | | | |
|---|---|---|---|---|---|---|---|---|---|---|---|---|---|---|
| | IV-21 | IV-22 | IV-23 | IV-24 | IV-25 | IV-26 | IV-27 | IV-28 | IV-29 | IV-30 | IV-31 | IV-32 | IV-33 | IV-34 |
| Curability[1] | ⊙ | ⊙ | ⊙ | ⊙ | ⊙ | ⊙ | ⊙ | ○ | ○ | ⊙ | ⊙ | ⊙ | ○ | ⊙ |
| Storage stability[2] | ○ | ○ | ○ | ○ | ○ | ○ | ○ | ○ | ○ | ○ | ○ | ○ | Δ | x |

[1]Film appearance after the MEK rubbing test (100 reciprocations).
⊙: No change; ○: Slightly changed; Δ: Whitening; x: Dissolved
[2]Viscosity increase after storing in a closed system at 40° C. for 2 weeks.
⊙: No change; ○: Slightly increased; Δ: increased; x: Gelling;

We claim:
1. A heat-curable resinous composition comprising:
(a) a hydroxy group-containing, film-forming resin;
(b) an amount of a melamine resin at a ratio on solids basis relative to said film-forming resin of 50:50 to 5:95, and
(c) 0.01 to 10% by weight relative to the cumulative amount of said film-forming resin and said melamine resin on solids basis of a compound of the formula:

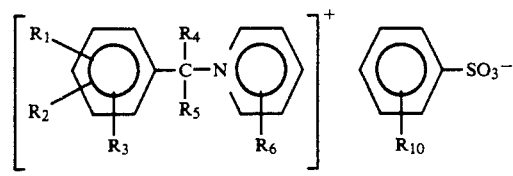

or

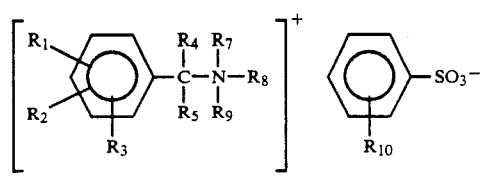

wherein $R_1$, $R_2$, $R_3$ and $R_6$ are each H, halogen, an alkyl, an alkoxy, nitro, amino, an alkylamino, cyano, an alkoxycarbonyl or carbamoyl; $R_4$ and $R_5$ are each H, an alkyl or halogen; $R_7$, $R_8$ and $R_9$ are each an alkyl, an alkenyl or phenyl which may be substituted with nitro, cyano, amino, halgen, an alkyl or a dialkylamino; and R10 is H or an alkyl.

2. The heat-curable resinous composition according to claim 1, wherein said hydroxy group-containing, film-forming resin is a hydroxy group-containing polyester resin, a hydroxy group-terminated polylactone resin, an epoxy resin or a hydroxy group-containing acrylic resin.